(12) United States Patent
Tsai et al.

(10) Patent No.: US 6,858,327 B2
(45) Date of Patent: Feb. 22, 2005

(54) ORGANIC LIGHT EMITTING MATERIALS AND DEVICES

(75) Inventors: Jui-Yi Tsai, Monroeville, PA (US);
Robert W. Walters, Export, PA (US);
Michael Barone, Pittsburgh, PA (US)

(73) Assignee: Universal Display Corporation, Ewing, NJ (US)

( * ) Notice: Subject to any disclaimer, the term of this patent is extended or adjusted under 35 U.S.C. 154(b) by 0 days.

(21) Appl. No.: 10/290,656

(22) Filed: Nov. 8, 2002

(65) Prior Publication Data

US 2004/0091738 A1 May 13, 2004

(51) Int. Cl.[7] .................. H05B 33/14; C09K 11/06; C07D 417/14

(52) U.S. Cl. .................. 428/690; 428/917; 313/504; 252/301.16; 546/2; 548/101

(58) Field of Search .................. 428/690, 917; 313/504, 506; 252/301.16; 257/102, 103; 546/2, 4; 548/101, 108

(56) References Cited

U.S. PATENT DOCUMENTS

| | | | |
|---|---|---|---|
| 4,769,292 A | 9/1988 | Tang et al. | 428/690 |
| 5,247,190 A | 9/1993 | Friend et al. | 257/40 |
| 5,703,436 A | 12/1997 | Forrest et al. | 313/506 |
| 5,707,745 A | 1/1998 | Forrest et al. | 428/432 |
| 5,834,893 A | 11/1998 | Bulovic et al. | 313/506 |

(List continued on next page.)

OTHER PUBLICATIONS

M. A. Baldo, et al., "Highly efficient phosphorescent emission from organic electroluminescent devices," Nature, Sep. 1998, vol. 395, pp. 151–154.

(List continued on next page.)

Primary Examiner—Marie Yamnitzky
(74) Attorney, Agent, or Firm—Kenyon & Kenyon

(57) ABSTRACT

Emissive materials are provided having the following structures:

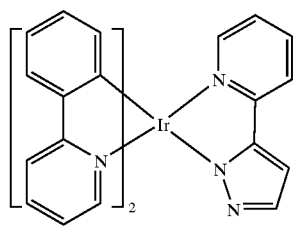

Compound 1

-continued

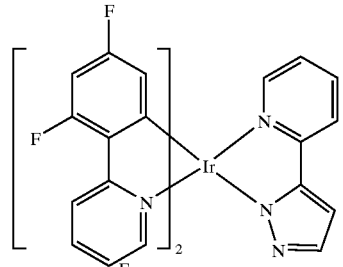

Compound 2

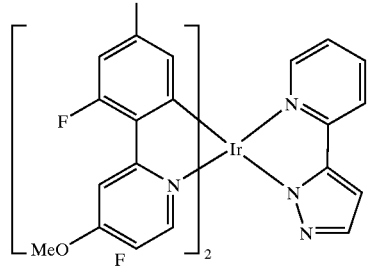

Compound 3

Compound 4

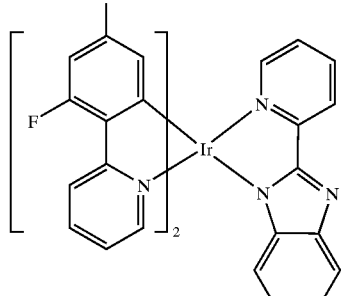

Compound 5

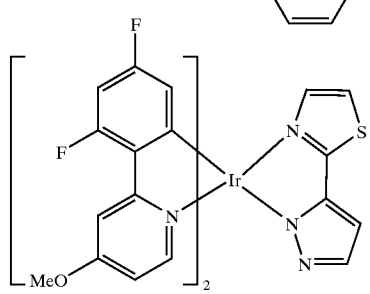

Compound 6

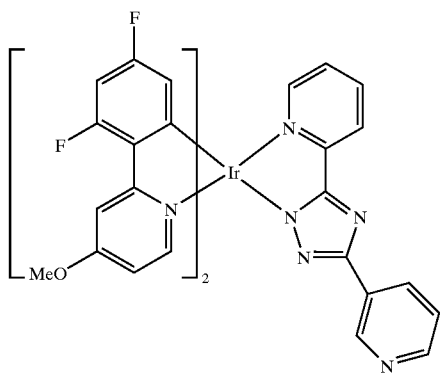

Devices incorporating the emissive materials are also provided.

2 Claims, 6 Drawing Sheets

U.S. PATENT DOCUMENTS

| | | | |
|---|---|---|---|
| 5,844,363 A | 12/1998 | Gu et al. | 313/506 |
| 6,013,982 A | 1/2000 | Thompson et al. | 313/506 |
| 6,087,196 A | 7/2000 | Sturm et al. | 438/29 |
| 6,091,195 A | 7/2000 | Forrest et al. | 313/504 |
| 6,097,147 A | 8/2000 | Baldo et al. | 313/506 |
| 6,294,398 B1 | 9/2001 | Kim et al. | 438/22 |
| 6,303,238 B1 | 10/2001 | Thompson et al. | 428/690 |
| 6,337,102 B1 | 1/2002 | Forrest et al. | 427/64 |
| 6,468,819 B1 | 10/2002 | Kim et al. | 438/22 |
| 6,565,994 B2 * | 5/2003 | Igarashi | 428/690 |
| 2002/0134984 A1 | 9/2002 | Igarashi | 257/79 |
| 2003/0230980 A1 | 12/2003 | Forrest et al. | 313/600 |

OTHER PUBLICATIONS

M.A. Baldo, et al., "Very high–efficiency green organic light–emitting devices based on electrophosphorescence", Applied Physics Letters, vol. 75, No. 1, pp. 4–6, Jul. 5, 1999.

C. Adachi, et al., "Nearly 100% internal phosphorescence efficiency in an organic light emitting device", J. Appl. Phys. 90, pp. 5048–5051, Nov. 2001.

* cited by examiner

ORGANIC LIGHT EMITTING MATERIALS AND DEVICES

RESEARCH AGREEMENTS

The claimed invention was made by, on behalf of, and/or in connection with one or more of the following parties to a joint university-corporation research agreement: Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs), and more specifically to organic materials used in such devices.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

OLED devices are generally (but not always) intended to emit light through at least one of the electrodes, and one or more transparent electrodes may be useful in an organic opto-electronic devices. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. For a device intended to emit light only through the bottom electrode, the top electrode does not need to be transparent, and may be comprised of a thick and reflective metal layer having a high electrical conductivity. Similarly, for a device intended to emit light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices may also be fabricated, where both electrodes are transparent. Side emitting OLEDs may also be fabricated, and one or both electrodes may be opaque or reflective in such devices.

As used herein, "top" means furthest away from the substrate, while "bottom" means closest to the substrate. For example, for a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

SUMMARY OF THE INVENTION

Emissive materials are provided having the following structures:

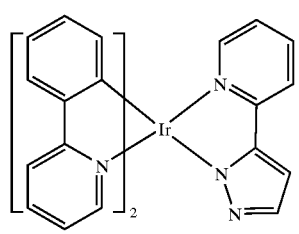

Compound 1

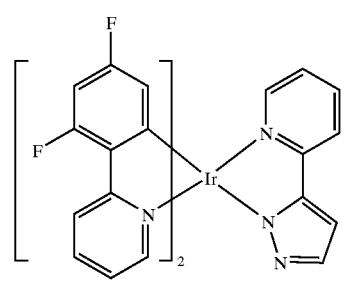

Compound 2

-continued

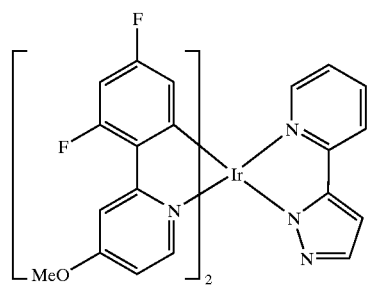

Compound 3

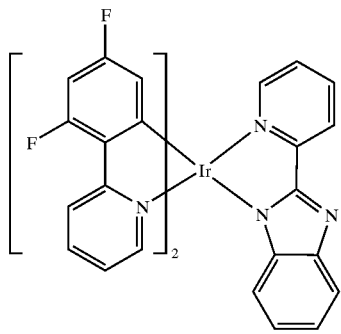

Compound 4

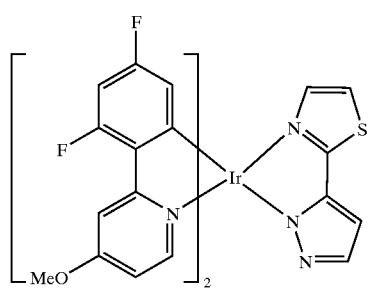

Compound 5

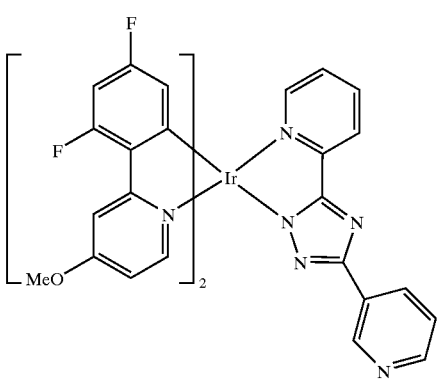

Compound 6

Devices incorporating the emissive materials are also provided.

DETAILED DESCRIPTION

Figure 1:
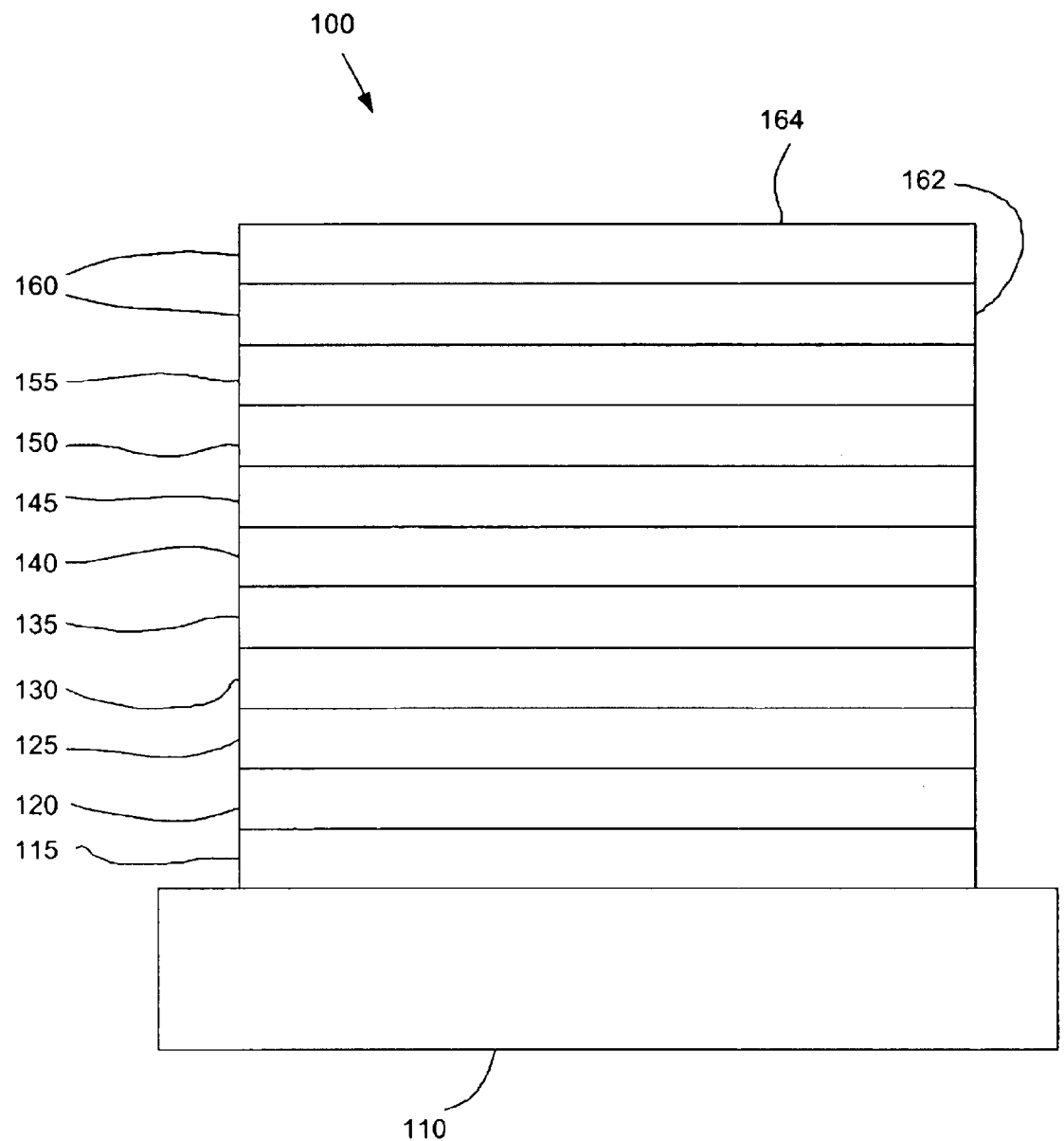
FIG. 1 shows an organic light emitting device having separate electron transport, hole transport, and emissive layers, as well as other layers.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices", Nature, vol. 395, 151–154, 1998; ("Baldo-I") and Baldo et al., "Very high-efficiency green organic light-emitting devices based on electrophosphorescence", Appl. Phys. Lett., vol. 75, No. 3, 4–6(1999) ("Baldo-II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a nonradiative mechanism, such that no light is emitted. Organic phosphorescence is also often observed in molecules containing heteroatoms with unshared pairs of electrons at very low temperatures. 2,2'-bipyridine is such a molecule. Non-radiative decay mechanisms are typically temperature dependent, such that a material that exhibits phosphorescence at liquid nitrogen temperatures may not exhibit phosphorescence at room temperature. But, as demonstrated by Baldo, this problem may be addressed by selecting phosphorescent compounds that do phosphoresce at room temperature.

Generally, the excitons in an OLED are believed to be created in a ratio of about 3:1, i.e., approximately 75% triplets and 25% singlets. See, Adachi et al., "Nearly 100% Internal Phosphorescent Efficiency In An Organic Light Emitting Device," J. Appl. Phys., 90, 5048 (2001), which is incorporated by reference in its entirety. In many cases, singlet excitons may readily transfer their energy to triplet excited states via "intersystem crossing," whereas triplet excitons may not readily transfer their energy to singlet excited states. As a result, 100% internal quantum efficiency is theoretically possible with phosphorescent OLEDs. In a fluorescent device, the energy of triplet excitons is generally lost to radiationless decay processes that heat-up the device, resulting in much lower internal quantum efficiencies. OLEDs utilizing phosphorescent materials that emit from triplet excited states are disclosed, for example, in U.S. Pat. No. 6,303,238, which is incorporated by reference in its entirety.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin-orbit coupling. Such a phosphorescent transition may be observed from an excited metal-to-ligand charge transfer (MLCT) state of an organometallic molecule such as tris(2-phenylpyridine)iridium(III).

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order.

Substrate 110 may be any suitable substrate that provides desired structural properties. Substrate 110 may be flexible or rigid. Substrate 110 may be transparent, translucent or opaque. Plastic and glass are examples of preferred rigid substrate materials. Plastic and metal foils are examples of preferred flexible substrate materials. Substrate 110 may be a semiconductor material in order to facilitate the fabrication of circuitry. For example, substrate 110 may be a silicon wafer upon which circuits are fabricated, capable of controlling OLEDs subsequently deposited on the substrate. Other substrates may be used. The material and thickness of substrate 110 may be chosen to obtain desired structural and optical properties.

Anode 115 may be any suitable anode that is sufficiently conductive to transport holes to the organic layers. The material of anode 115 preferably has a work function higher than about 4 eV (a "high work function material"). Preferred anode materials include conductive metal oxides, such as indium tin oxide (ITO) and indium zinc oxide (IZO), aluminum zinc oxide (AlZnO), and metals. Anode 115 (and substrate 110) may be sufficiently transparent to create a bottom-emitting device. A preferred transparent substrate and anode combination is commercially available ITO (anode) deposited on glass or plastic (substrate). A flexible and transparent substrate-anode combination is disclosed in U.S. Pat. No. 5,844,363, which is incorporated by reference in its entirety. Anode 115 may be opaque and/or reflective. A reflective anode 115 may be preferred for some top-emitting devices, to increase the amount of light emitted from the top of the device. The material and thickness of anode 115 may be chosen to obtain desired conductive and optical properties. Where anode 115 is transparent, there may be a range of thickness for a particular material that is thick enough to provide the desired conductivity, yet thin enough to provide the desired degree of transparency. Other anode materials and structures may be used.

Hole transport layer 125 may include a material capable of transporting holes. Hole transport layer 130 may be intrinsic (undoped), or doped. Doping may be used to enhance conductivity. α-NPD and TPD are examples of intrinsic hole transport layers. An example of a p-doped hole transport layer is m-MTDATA doped with $F_4$-TCNQ at a molar ratio of 50:1, as disclosed in U.S. patent application Ser. No. 2003/0230980, which is incorporated by reference in its entirety. Other hole transport layers may be used.

Emissive layer 135 may include an organic material capable of emitting light when a current is passed between anode 115 and cathode 160. Preferably, emissive layer 135 contains a phosphorescent emissive material, although fluorescent emissive materials may also be used. Phosphorescent materials are preferred because of the higher luminescent efficiencies associated with such materials. Emissive layer 135 may also comprise a host material capable of transporting electrons and/or holes, doped with an emissive material that may trap electrons, holes, and/or excitons, such that excitons relax from the emissive material via a photoemissive mechanism. Emissive layer 135 may comprise a single material that combines transport and emissive properties. Whether the emissive material is a dopant or a major constituent, emissive layer 135 may comprise other materials, such as dopants that tune the emission of the emissive material. Emissive layer 135 may include a plurality of emissive materials capable of, in combination, emitting a desired spectrum of light. Examples of phosphorescent emissive materials include $Ir(ppy)_3$. Examples of fluorescent emissive materials include DCM and DMQA. Examples of host materials include $Alq_3$, CBP and mCP. Examples of emissive and host materials are disclosed in U.S. Pat. No. 6,303,238 to Thompson et al., which is incorporated by reference in its entirety. Emissive material may be included in emissive layer 135 in a number of ways. For example, an emissive small molecule may be incorporated into a polymer or dendrimer molecule. Other emissive layer materials and structures may be used.

Electron transport layer 140 may include a material capable of transporting electrons. Electron transport layer 140 may be intrinsic (undoped), or doped. Doping may be used to enhance conductivity. $Alq_3$ is an example of an intrinsic electron transport layer. An example of an n-doped electron transport layer is BPhen doped with Li at a molar ratio of 1:1, as disclosed in U.S. patent application Ser. No. 2003/0230980, which is incorporated by reference in its entirety. Other electron transport layers may be used.

Cathode 160 may be any suitable material or combination of materials known to the art, such that cathode 160 is capable of conducting electrons and injecting them into the organic layers of device 100. Cathode 160 may be transparent or opaque, and may be reflective. Metals and metal oxides are examples of suitable cathode materials. Cathode 160 may be a single layer, or may have a compound structure. FIG. 1 shows a compound cathode 160 having a thin metal layer 162 and a thicker conductive metal oxide layer 164. In a compound cathode, preferred materials for the thicker layer 164 include ITO, IZO, and other materials known to the art. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The part of cathode 160 that is in contact with the underlying organic layer, whether it is a single layer cathode 160, the thin metal layer 162 of a compound cathode, or some other part, is preferably made of a material having a work function lower than about 4 eV (a "low work function material"). Other cathode materials and structures may be used.

Blocking layers may be used to reduce the number of charge carriers (electrons or holes) and/or excitons that leave the emissive layer. An electron blocking layer 130 may be disposed between emissive layer 135 and the hole transport layer 125, to block electrons from leaving emissive layer 135 in the direction of hole transport layer 125. Similarly, a hole blocking layer 140 may be disposed between emissive layer 135 and electron transport layer 145, to block holes from leaving emissive layer 135 in the direction of electron transport layer 140. Blocking layers may also be used to block excitons from diffusing out of the emissive layer. The theory and use of blocking layers is described in more detail in U.S. Pat. No. 6,097,147 and U.S. patent application Ser. No. 2003/0230980, which are incorporated by reference in their entireties.

Generally, injection layers are comprised of a material that may improve the injection of charge carriers from one layer, such as an electrode or an organic layer, into an adjacent organic layer. Injection layers may also perform a charge transport function. In device 100, hole injection layer 120 maybe any layer that improves the injection of holes from anode 115 into hole transport layer 125. CuPc is an example of a material that may be used as a hole injection layer from an ITO anode 115, and other anodes. In device 100, electron injection layer 150 may be any layer that improves the injection of electrons into electron transport layer 145. LiF/Al is an example of a material that may be used as an electron injection layer into an electron transport layer from an adjacent layer. Other materials or combinations of materials may be used for injection layers. Depending upon the configuration of a particular device, injection layers may be disposed at locations different than those shown in device 100. More examples of injection layers are provided in U.S. patent application Ser. No. 09/931,948 to Lu et al., which is incorporated by reference in its entirety.

A protective layer may be used to protect underlying layers during subsequent fabrication processes. For example, the processes used to fabricate metal or metal oxide top electrodes may damage organic layers, and a protective layer may be used to reduce or eliminate such damage. In device 100, protective layer 155 may reduce damage to underlying organic layers during the fabrication of cathode 160. Preferably, a protective layer has a high carrier mobility for the type of carrier that it transports (electrons in device 100), such that it does not significantly increase the operating voltage of device 100. CuPc, BCP, and various metal phthalocyanines are examples of materials that may be used in protective layers. Other materials or combinations of materials may be used. The thickness of protective layer 155 is preferably thick enough that there is little or no damage to underlying layers due to fabrication processes that occur after organic protective layer 160 is deposited, yet not so thick as to significantly increase the operating voltage of device 100. Protective layer 155 may be doped to increase its conductivity. For example, a CuPc or BCP protective layer 160 may be doped with Li. A more detailed description of protective layers may be found in U.S. patent application Ser. No. 09/931,948 to Lu et al., which is incorporated by reference in its entirety.

Figure 2:
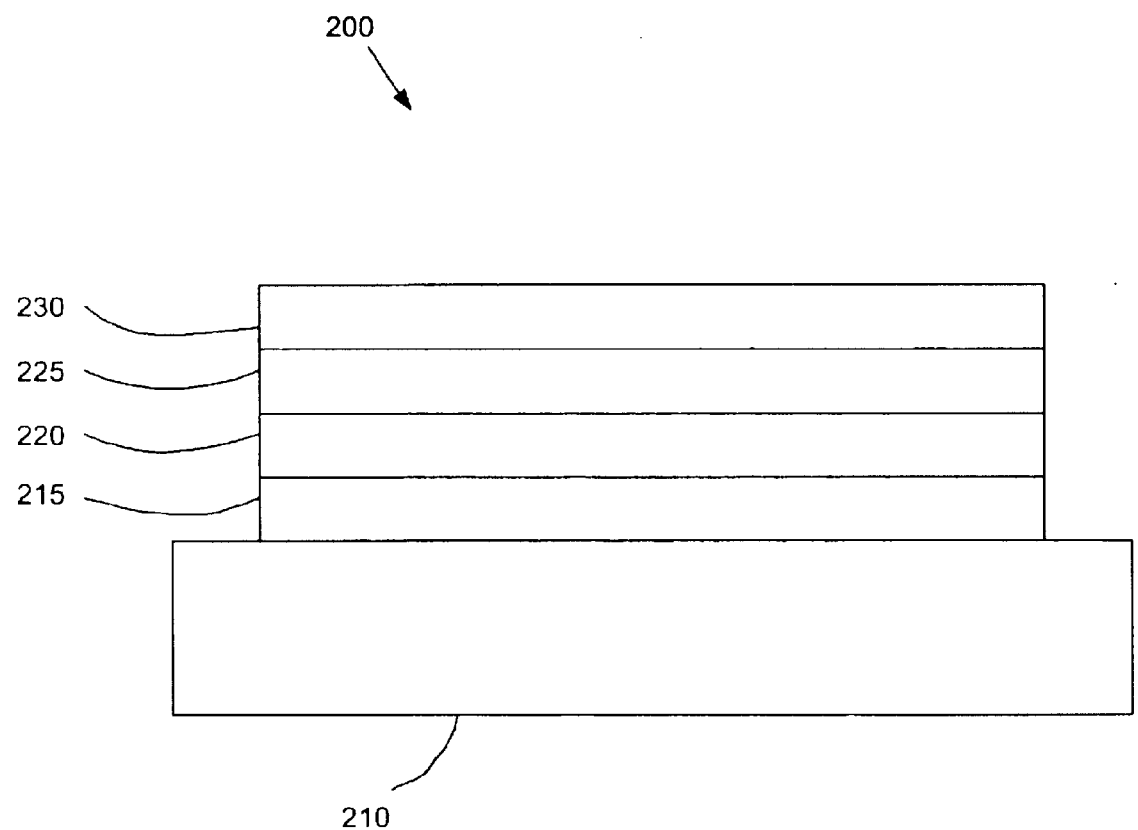
FIG. 2 shows an inverted organic light emitting device that does not have a separate electron transport layer.

FIG. 2 shows an inverted OLED 200. The device includes a substrate 210, an cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190, Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and organic vapor jet deposition (OVJD), such as described in U.S. patent application Ser. No. 10/233,470. Other suitable deposition methods include spin coating and other solution based processes. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20–25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

In one embodiment of the invention, an emissive material is provided having the structure of Formula 1:

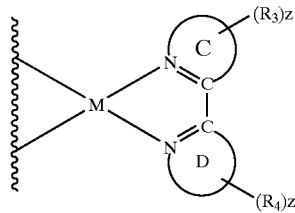

where M may be a heavy metal with an atomic weight of greater than 40. $R_3$ and $R_4$ may be independently selected from the group consisting of H, halogens, CN, $CF_3$, $C_nF_{2n+1}$, trifluorovinyl, $NO_2$, $CO_2R$, $C(O)R$, $C\equiv CR$, alkyl, alkenyl, amino, aryl, heteroaryl, aryl or heteroaryl groups substituted with halogens, CN, $CF_3$, $CnF_{2n+1}$, trifluorovinyl, $NO_2$, $CO_2R$, $C(O)R$, OR, SR, $NR_2$ (including cyclic-amino), where R is hydrogen, an alkyl group, an aryl group or a heteroaryl group, wherein z represents an integer from 1 to 4. The ring system designated by C or D may independently be a 5 or 6-membered aryl or heteroaryl ring system. C and D may incorporate a single or multiple heteroatom. Examples of such heteroatoms include nitrogen, sulfur or oxygen groups or any combination thereof. Where z is greater than one, the individual substituents on a particular ring may be the same or may be different. Substituents may be linked with other substituents.

In preferred embodiments $R_3$ and $R_4$ are independently selected from the group consisting of hydrogen, alkyl, alkoxy, amino, trifluoromethyl, halogen, aryl, heteroaryl. In a most preferred embodiment $R_3$ and $R_4$ are independently selected from the group consisting of H, methyl, F and methoxy.

In a further preferred embodiment of the present invention, an emissive material is provided having the structure of Formula 2:

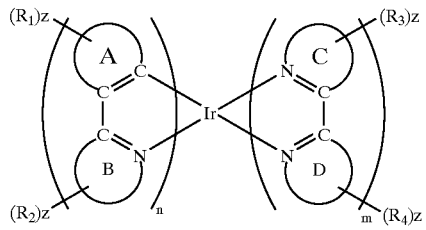

Rings A, B C and D may be independently selected from the group consisting of 5 or 6-membered aryl or heteroaryl ring system. $R_1$, $R_2$, $R_3$ and $R_4$ each represent one or more substituents on the 5 or 6-membered rings, wherein z represents an integer from 0 to 4, n represents an integer from 0 to 2 and m represents an integer from 1 to 3. A, B, C or D may incorporate a single or multiple heteroatom. Examples of such heteroatoms include nitrogen, sulphur or oxygen groups or any combination thereof. Where z is greater than one, the individual substituents on a particular ring may be the same or may be different.

In a preferred embodiment $R_1$, $R_2$, $R_3$ and $R_4$ are independently selected from the group consisting of H, halogens, CN, $CF_3$, $C_nF_{2n+1}$, trifluorovinyl, $NO_2$, $CO_2R$, $C(O)R$, $C\equiv CR$, alkyl, alkenyl, aryl, heteroaryl, aryl or heteroaryl groups, which may be further substituted with halogens, CN, $CF_3$, $C_nF_{2n+1}$, trifluorovinyl, $NO_2$, $CO_2R$, $C(O)R$, OR, SR, $NR_2$ (including cyclic-amino), where R is hydrogen, an alkyl group, an aryl group or a heteroaryl group. In a more preferred embodiment $R_1$, $R_2$, $R_3$ and $R_4$ are independently selected from the group consisting of H, alkyl, alkoxy, amino, halogen, aryl, heteroaryl. In a most preferred embodiment $R_1$, $R_2$, $R_3$ and $R_4$ are independently selected from the group consisting of H, F and methoxy.

In one preferred embodiment, individual substituents in $R_1$, $R_2$, $R_3$, and/or $R_4$ may be linked to form a fused saturated, aryl, or heteroaryl ring system.

The organometallic compounds comprise a heavy transition metal (designated M) which may produce phosphorescent emission from a mixture of MLCT and $\pi$-$\pi$* ligand states. Suitable transition metals include but are not limited to Ir, Pt, Pd, Rh, Re, Os, Ti, Pb, Bi, In, Sn, Sb, Te, Au, and Ag and other heavy metals with an atomic number of at least 40. Preferably the atomic number is at least 72. The metal may be bound to at least one mono-anionic, bidentate, carbon-coordination ligand substituted with electron donating and/or electron withdrawing substituents that shift the emission, relative to the un-substituted ligand, to either the blue, green or red region of the visible spectrum. In embodiments of the present invention, the at least one mono-anionic, bidentate, carbon-coordination ligand may be substituted with at least one electron withdrawing or electron donating substituent. Further, the metal may be bound to at least one other monoanionic ligand that is different to the first mono-anionic, bidentate, carbon coordination ligand.

Embodiments of the invention have been represented as monomeric structure. The compounds may also be present as dimers, trimers or dendrimers.

Aryl alone or in combination includes carbocyclic aromatic systems or heterocyclic aromatic systems (also known as heteroaryl). The systems may contain one, two or three rings wherein each ring may be attached together in a pendent manner or may be fused. Preferably the rings have 5 or 6 members.

Alkyl alone or in combination includes linear or branched alkyl groups, preferably $C_1$ to $C_6$ alkyl groups, more preferably $C_1$ to $C_3$ alkyl groups.

Substituted refers to any level of substitution although mono-, di- and tri-substitutions are preferred.

In a preferred embodiment, novel organic emissive layers are provided. These layers may include materials selected from the group consisting of:

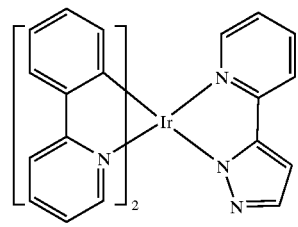

Compound 1

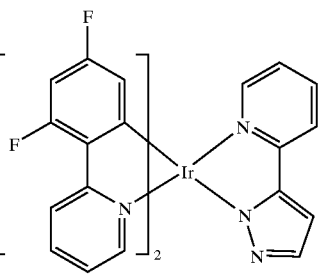

Compound 2

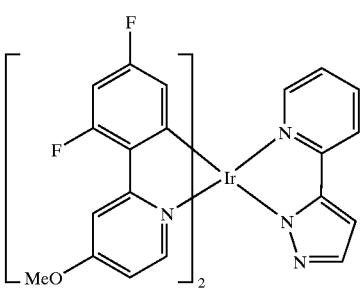

Compound 3

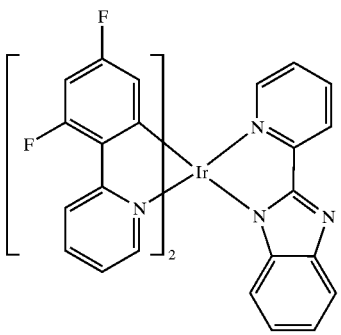

Compound 4

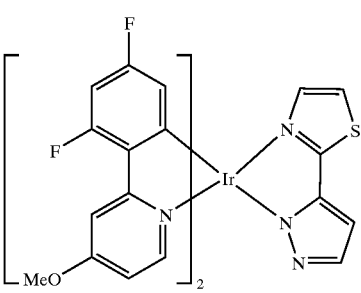

Compound 5

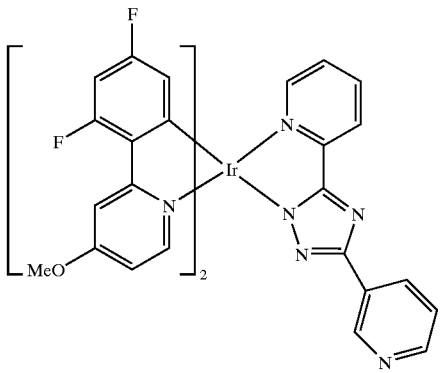

Compound 6

It is understood that the various embodiments described herein are by way of example only, and are not intended to limit the scope of the invention. For example, many of the materials and structures described herein may be substituted with other materials and structures without deviating from the spirit of the invention. It is understood that various theories as to why the invention works are not intended to be limiting. For example, theories relating to charge transfer are not intended to be limiting.

Material Definitions

As used herein, abbreviations refer to materials as follows:

| | |
|---|---|
| CBP: | 4,4'-N,N'dicarbazole-biphenyl |
| m-MTDATA | 4,4',4"-tris(3-methylphenylphenlyamino)triphenylamine |
| Alq$_3$: | 8-tris-hydroxyquinoline aluminum |
| Bphen: | 4,7-diphenyl-1,10-phenanthroline |
| n-BPhen: | n-doped BPhen (doped with lithium) |
| F$_4$-TCNQ: | tetrafluoro-tetracyano-quinodimethane |
| p-MTDATA: | p-doped m-MTDATA (doped with F4-TCNQ) |
| Ir(ppy)$_3$: | tris(2-phenylpyridine)-iridium |
| Ir(ppz)$_3$: | tris(1-phenylpyrazoloto,N,C(2')iridium(III) |
| BCP: | 2,9-dimethyl-4,7-diphenyl-1,10-phenanthroline |
| TAZ: | 3-phenyl-4-(1'-naphthyl)-5-phenyl-1,2,4-triazole |
| CuPc: | copper phthalocyanine. |
| ITO: | indium tin oxide |
| NPD: | naphthyl-phenyl-diamine |
| TPD: | N,N'-bis(3-methylphenyl)-N,N'-bis-(phenyl)-benzidine |
| BAlq: | aluminum(III)bis(2-methyl-8-quinolinato)4-phenylphenolate |
| mCP: | 1,3-N-N'-dicarbazole-benzene |
| DCM: | 4-(dicyanoethylene)-6-(4-dimethylaminostyryl-2-methyl)-4H-pyran |
| DMQA: | N,N'-dimethylquinacridone |
| FIrpic: | iridium(III)bis[(4,6-di-fluorophenyl)-pyridinato-N,,C$^{2'}$] picolinate |

Experimental

Specific representative embodiments of the invention will now be described, including how such embodiments may be made. It is understood that the specific methods, materials, conditions, process parameters, apparatus and the like do not necessarily limit the scope of the invention.

Several compounds were synthesized in accordance with embodiments of the invention. Compounds 1 through 6, as illustrated earlier, were synthesized. The following results were observed for exemplary compounds of the present invention.

| Compound | Emission (λ max nm) | CIE (x, y) in $CH_2Cl_2$ |
|---|---|---|
| 1 | 491, 517 nm | (0.23, 0.56) |
| 2 | 459, 487 nm | (0.16, 0.27) |
| 3 | 454, 482 nm | (0.16, 0.24) |
| 4 | 519 nm | (0.30, 0.53) |
| 5 | 483, 508 | nd |
| 6 | 481 nm | (0.17, 0.29) |

Compounds 1 through 6 were synthesized as follows:
Compound 1
Step 1
2-Phenylpyridine (15.5 g, 0.1 mol) and Iridium(III) chloride hydrate (18.5 g, 50 mmol.) were added to a flask containing 300 mL. of 2-methoxyethanol and 75 mL. of distilled water. The reaction mixture was heated to reflux and stirred under a nitrogen atmosphere for 24 hours. After cooling, the yellow precipitate was vacuum filtered and washed first with absolute ethanol followed by hexanes. The product [2-phenylpyridine]₂Ir₂(u-cl)₂[2-phenylpyridine]₂ was dried in a vacuum oven to give 20 g (74% yield). The product was not purified any further but used directly in the next step.
Step 2
2-Acetylpyridine (48.28 g, 0.398 mole) and N,N-Dimethylformamide dimethyl acetal (95 g. 0.797 mole) were added to a flask. The reaction mixture was heated to 104° C. for 15 hours. The excess N,N-Dimethylformamide dimethyl acetal was evaporated off. The residue was recrystallized from a mixture of toluene (140 mL.) and heptane (955 mL.) to give 1-(2-pyridyl)-3-dimethylamino-2-propen-1-one (58.7 g, 70% yield).
Step 3
1-(2-Pyridyl)-3-dimethylamino-2-propen-1-one (25 g, 0.12 mole) and hydrazine hydrate (7.81 g, 0.156 mole) were added to a flask containing 250 mL. of absolute ethanol (250 mL.). The reaction mixture was heated to 78° C. for 14 hours. The reaction mixture was concentrated, and the residue was subjected to kugelrohr distillation. The crude product was distillated at 190° C. at 0.45 torr to give 2-pyrazol-pyridine (17.3 g, 99% yield).
Step 4
[2-phenyl-pyridine]₂Ir₂(u-cl)₂[2-phenyl-pyridine]₂ (6 g, 6.64 mmole) was dissolved in 163 mL. methylene chloride and 163 mL. methanol. AgOTf (2.89 g, 11.28 mmole) was added to yield a cream-colored slurry. After the slurry was stirred for 2 hours at room temperature, it was filtered and the filtrate was evaporated to dryness to yield a yellow, oily residue. The residue was dissolved in 163 mL. $CH_3CN$, and 2-pyrazol-pyridine Na salt (prepared from 1.63 g of 2-pyrazol-pyridine from step 3 above and 284 mg of sodium hydride) was added to the solution. After the solution was heated at 81 C. for 18 hours under nitrogen, it was filtered. The precipitate was further purified by column chromatography ($Al_2O_3$, basic, 150 mesh) with the elution of solvent mixture ($CH_2Cl_2$: MeOH=59:1). Compound 1 was obtained with 58% yield (4.2 g)
Compound 2
Step 1
2-Bromopyridine (20.01 g, 0.126 mole), 2',4'-difluorophenylboronic acid (24 g, 0.152 mole), triphenylphosphine (3.32 g, 0.0126 mole), palladium acetate (0.71 g, 0.003165 mole) and a 2M aqueous solution of potassium carbonate (170 mL.) were added to a flask containing 200 mL. of 1,2-dimethoxyethane. The reaction mixture was heated to reflux and stirred under a nitrogen atmosphere for 24 hours. After cooling, the aqueous phase was separated and extracted by ethyl acetate. The organic phases were combined, dried over magnesium sulfate, and evaporated to dryness. The residue was subject to kugelrohr distillation. 2-(2',4'-difluorophenyl)-pyridine was distilled at 150° C. under the vaccum of 0.4 torr. (24.1 g, 99%).
Step 2
2-(2',4'-Difluorophenyl)pyridine (1.02 g, 5.33 mmol) and Iridium(III) chloride hydrate (0.47 g, 1.33 mmol.) were added to a flask containing 30 mL. of 2-methoxyethanol and 7.5 mL. of distilled water. The reaction mixture was heated to reflux and stirred under a nitrogen atmosphere for 24 hours. After cooling, the yellow precipitate formed was vacuum filtered and washed first with absolute ethanol followed by hexanes. The dichloro-bridged dimer was dried in a vacuum oven to give the crude product [2-(4',6'-Difluorophenyl)-pyridine]₂Ir₂(u-cl)₂[2-(4',6'-difluorophenyl)-pyridine]₂ (0.56 g, 83% yield). The product was not purified any further but used directly in the next step.
Step 3
[2-(4',6'-difluorophenyl)-pyridine]₂Ir₂(u-cl)₂[2-(4',6'-difluororophenyl)-pyridine]₂ (4.18 g, 3.445 mmole) was dissolved in 100 mL. methylene chloride and 100 mL. methanol. AgOTf (1.77 g, 6.89 mmole) was added to yield a cream-colored slurry. After the slurry was stirred for 2 hours at room temperature, it was filtered and the filtrate was evaporated to dryness to yield a yellow, oily residue. The residue was dissolved in 100 mL. $CH_3CN$, and 2-pyrazol-pyridine Na salt (prepared from 1 g of 2-pyrazol-pyridine and 173.62 mg of sodium hydride) was added to the solution. The solution was heated and maintained at 81° C. for 18 hours under a nitrogen atmosphere. The precipitate that was filtered and was purified by column chromatography ($Al_2O_3$, basic, 150 mesh) with the elution of solvent mixture ($CH_2Cl_2$: MeOH=59:1) to give Compound (2) (3.51 g, 71% yield).
Compound 3
Step 1
Synthesis of 4-methoxy-2-bromopyridine
A solution of N,N-dimethylamine ethanol (78.086 g, 0.876 mole) in anhydrous hexanes(1241 mL.) was cooled to 0° C. and butyllithium (2M soln. 876 mL., 1.757 mole) was added by use of an addition funnel. After 30 minutes at 0° C., 4-methoxypyridine(47.87 g, 0.438 mole) was added. Stirring continued at 0° C. for one hour before the reaction mixture was cooled to −78° C. and a solution of $CBr_4$ (363 g, 1.093 mole) was added. The reaction temperature was maintained at 0° C. for 2.5 hours. The water was then added to quench the reaction. The aqueous layer was then separated and extracted with methylene chloride. The organic extractions were washed with brine, dried over magnesium sulfate and evaporated to give crude product. The crude product was purified by column chromatography using 80/20 ethyl acetate/hexanes as the eluants. The purified product was collected and concentrated to give 4-methoxy-2-bromopyridine (17 g. 22% yield).
Step 2
4-methoxy-2-bromopyridine (16.9 g, 89.8 mmole), 2',4'-difluorophenylbomic acid (17.02 g, 107.8 mmole), triphenylphosphine (2.35 g, 8.98 mmole), palladium acetate (0.504 g, 2.245 mmole) and Potassium carbonate (2M aqueous solution.; 121 mL.) were added to a flask containing 152 mL. of 1,2-dimethoxyethane. The reaction mixture was heated to reflux and stirred under a nitrogen atmosphere for 24 hours. After cooling, the aqueous phase was separated and extracted by ethyl acetate. The organic phase was combined and was dried over magnesium sulfate, then was evaporated to dryness. The residue was subject to kugelrohr distillation to give 2-(2',4'-difluorophenyl)-pyridine (16.7 g, 84.3%) at 195C under the vaccum of 0.4 torr.
Step 3
2-(2',4'-Difluorophenyl)-4-methoxypyridine (0.5 g, 2.25 mmol) and Iridium(III) chloride hydrate (0.417 g, 1.125 mmol.) were added to a flask containing 30 mL. of 2-methoxyethanol and 7.5 mL. of distilled water. The reaction mixture was heated to reflux and stirred under a nitrogen atmosphere for 24 hours. After cooling, the yellow precipitate formed was vacuum filtered and washed first with absolute ethanol followed by hexanes. The dichloro-bridged dimer was dried in a vacuum oven to give 0.625 g (83% yield). The product was not purified any further but used directly in the next step.

Step 4

[2-(4',6'-difluorophenyl)-4-methoxypyridine]$_2$Ir$_2$(u-cl)$_2$ [2-(4', 6'-difuorophenyl)-4-methoxypyridine]$_2$ (759 mg, 5.24 mmole) was dissolved in 76 mL. methylene chloride and 76 mL. methanol. AgOTf (1.34 g, 5.24 mmole) was added to yield a cream-colored slurry. After the slurry was stirred for 2 hours at room temperature, it was filtered and the filtrate was evaporated to dryness to yield a yellow, oily residue. The residue was dissolved in 76 mL. CH$_3$CN, and 2-pyrazol-pyridine Na salt (prepared from 0.759 g of 2-pyrazol-pyridine and 132 mg of sodium hydride) was added to the solution. After the solution was heated at 81 C. for 18 hours under nitrogen, it was filtered. PZPY3was obtained with 71% yield (2.89 g).

Compound 4

[2-(4',6'-Difluorophenyl)-pyridine]$_2$Ir$_2$(u-cl)$_2$[2-(4', 6'-difluorophenyl)-pyridine]$_2$ (150 mg, 0.1234 mmole) was dissolved in 4.5 mL. methylene chloride and 4.5 mL. methanol. AgOTf (63.4 mg, 0.2468 mmole) was added to yield a cream-colored slurry. After the slurry was stirred for 2 hours at room temperature, it was filtered and the filtrate was evaporated to dryness to yield a yellow, oily residue. The residue was dissolved in 4.5 mL. CH$_3$CN, and 2-benzimidazole-pyridine Na salt (prepared from 2 g of 2-pyrazol-pyridine and 258 mg of sodium hydride) was added to the solution. After the solution was heated at 81° C. for 18 hours under nitrogen, it was filtered to give (3) (0.124 g, 65% yield) as a solid.

Compound 5

[2-(4',6'-difluorophenyl)-4-methoxypyridine]$_2$Ir$_2$(u-cl)$_2$ [2-(4', 6'-difluorophenyl)-4-methoxypyridine]$_2$ (17.62 mg, 0.0132 mmole) was dissolved in 0.38 mL. of methylene chloride and 0.38 mL. methanol. AgOTf (6.782 mg, 0.0264 mmole) was added to yield a cream-colored slurry. After the slurry was stirred for 2 hours at room temperature, it was filtered and the filtrate was evaporated to dryness to yield a yellow, oily residue. The residue was dissolved in 0.38 mL. CH$_3$CN, and 2-(1H-pyrazole-3-yl)-1,3-thiazole sodium salt (prepared from 4 mg of 2-(1H-pyrazole-3-yl)-1,3-thiazole and 0.66 mg of sodium hydride) was added to the solution. After the solution was heated at 81° C. for 18 hours under nitrogen, it was filtered to give Compound 5.

Compound 6

[2-(4',6'-difluorophenyl)-4-methoxypyridine]$_2$Ir$_2$(u-cl)$_2$ [2-(4', 6'-difluorophenyl)-4-methoxypyridine]$_2$ (14.94 mg, 0.0111 mmole) was dissolved in 0.32 mL. methylene chloride and 0.32 mL. methanol. AgOTf (5.752 mg, 0.02239 mmole) was added. The slurry was stirred for 2 hours at room temperature, and evaporated to dryness to yield a yellow, oily residue. The residue was dissolved in 1 mL. CH$_3$CN, and 2-[5-(3-pyridyl)-1H-1,2,4-triazol-3-yl] pyridine sodium salt (prepared from 5 mg of 2-[5-(3-pyridyl)-1H-1,2,4-triazol-3-yl]pyridine and 0.5912 mg of sodium hydride) was added to the solution. After the solution was heated at 81° C. for 18 hours under nitrogen, it was filtered to give Compound 6.

Devices were fabricated incorporating compounds 1 and 2. The starting substrates were glass substrates coated with ITO of 130–150 nm thickness and sheet resistance <20 Ω/square, purchased from Applied Films Corporation. The substrates were degreased with solvents and cleaned with oxygen plasma and UV ozone treatments. All subsequent thin films were deposited by thermal evaporation at a pressure of <1×10$^{-6}$ Torr.

Device 1

First CuPc was deposited as a hole injection layer on the anode to a thickness of 10 nm at a rate of 0.3 Å/s. Next, NPD was deposited as a hole transport layer to a thickness of 30 nm at a rate of 1.5 Å/s. Next, CBP and compound 1 were co-evaporated from different sources to form a light emitting layer of 30 nm thickness. CBP was deposited at a rate of 1.6 Å/s, and compound 1 was incorporated into CBP at 6 wt %. Next, on the light emitting layer, BAlq$_2$ was deposited as a hole blocking layer to a thickness of 10 nm at a rate of 1.0 Å/s. Next, on the hole blocking layer, Alq$_3$ was deposited as an electron transporting layer to a thickness of 30 nm at a rate of 1.0 Å/s. Next, on the electron transport layer, lithium fluoride (LiF) was deposited as an electron injecting layer at a thickness of 0.5 nm at a rate of 0.5 Å/s. Lastly, aluminum (Al) was deposited on the electron injecting layer at a thickness of 100 nm at a rate of 2 Å/s to complete the organic light emitting device.

Device 2

First CuPc was deposited as a hole injection layer on the anode to a thickness of 10 nm at a rate of 0.3 Å/s. Next, NPD was deposited as a hole transport layer to a thickness of 30 nm at a rate of 1.5 Å/s. Next, mCP and compound 2 were co-evaporated from different sources to form a light emitting layer of 30 nm thickness. CBP was deposited at a rate of 1.6 Å/s, and Compound 2 was incorporated into CBP at 6 wt %. Next, on the light emitting layer, BAlq$_2$ was deposited as a hole blocking layer to a thickness of 40 nm at a rate of 1.0 Å/s. Next, on the hole blocking layer, lithium fluoride (LiF) was deposited as an electron injecting layer at a thickness of 0.5 nm at a rate of 0.5 Å/s. Lastly, aluminum (Al) was deposited on the electron injecting layer at a thickness of 100 nm at a rate of 2 Å/s to complete the organic light emitting device.

Figure 3:
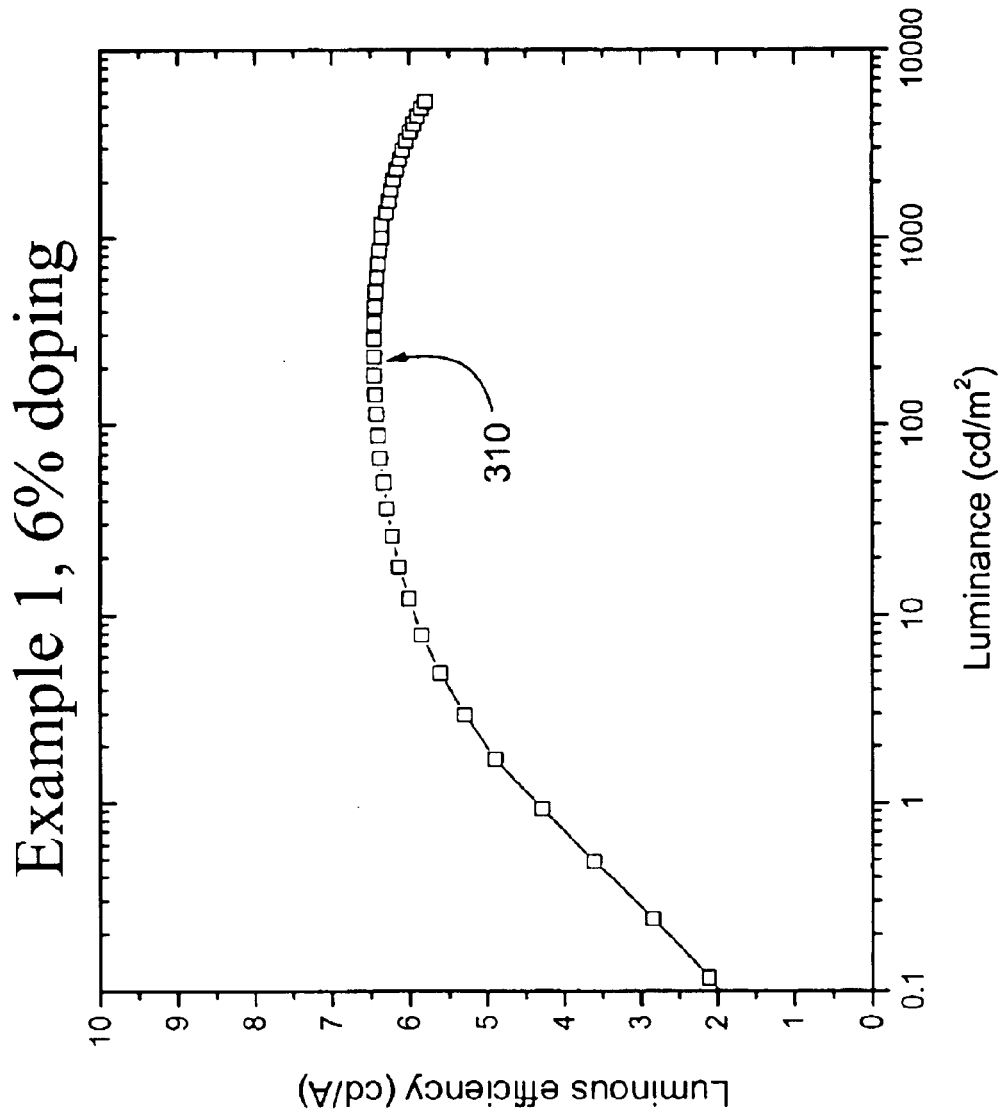
FIG. 3 shows a plot of luminous efficiency v. luminance for a device fabricated in accordance with an embodiment of the invention.
Figure 4:
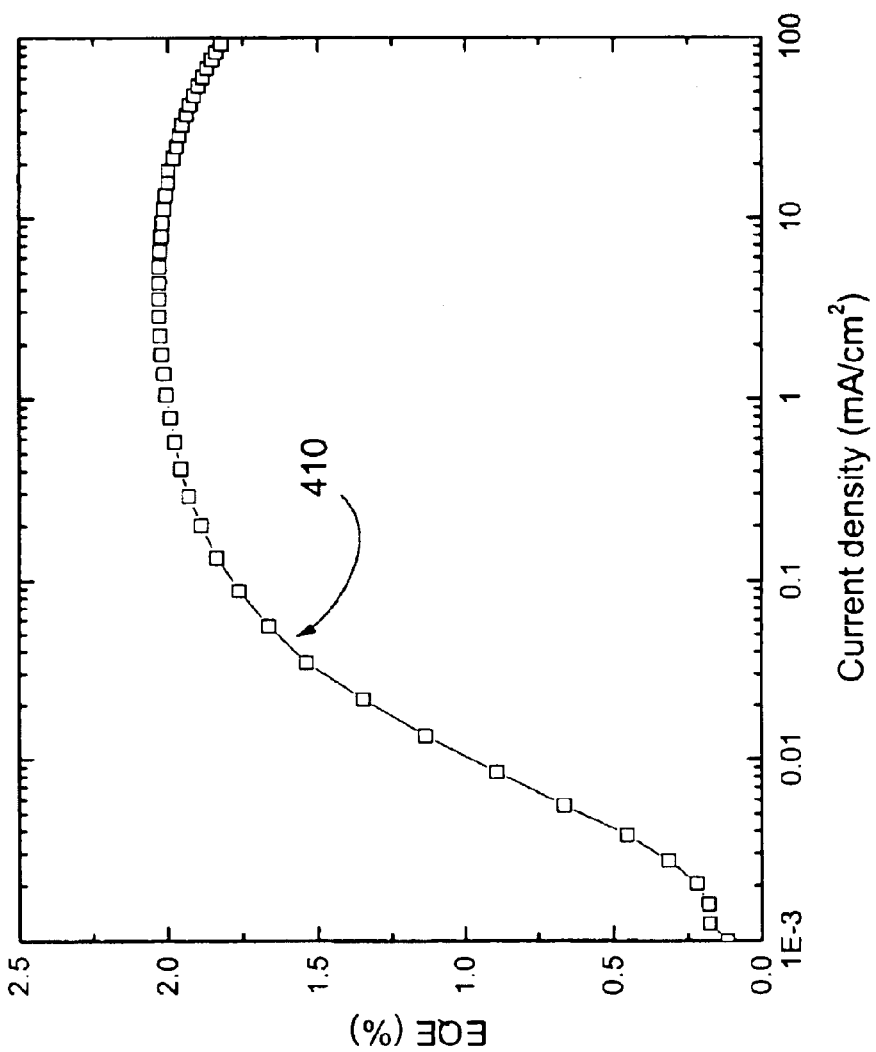
FIG. 4 shows a plot of external quantum efficiency v. current density for a device fabricated in accordance with an embodiment of the invention.
Figure 5:
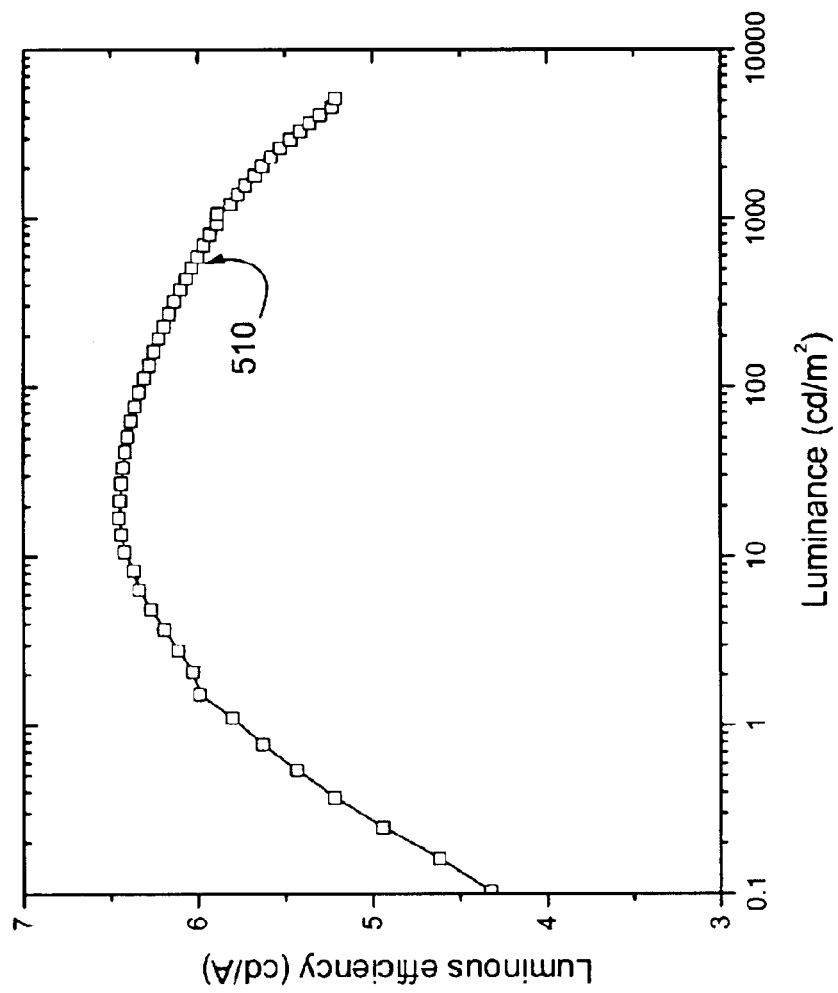
FIG. 5 shows a plot of luminous efficiency v. luminance for a device fabricated in accordance with an embodiment of the invention.
Figure 6:
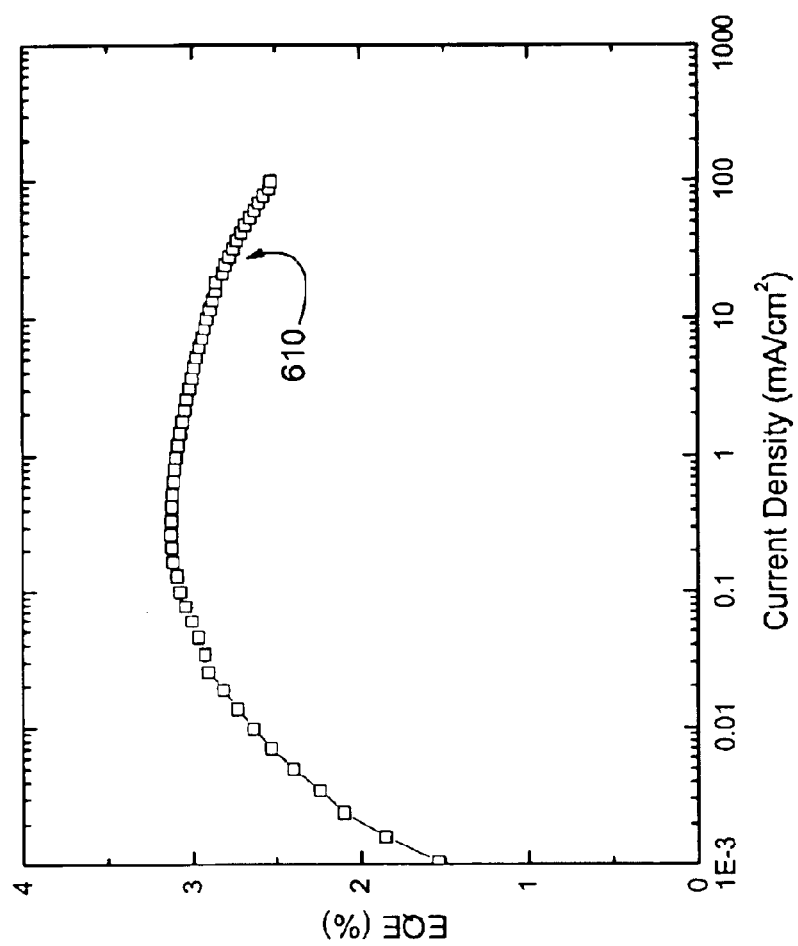
FIG. 6 shows a plot of external quantum efficiency v. current density for a device fabricated in accordance with an embodiment of the invention.

The devices were characterized by measuring current-voltage and luminance characteristics, as well as spectral output characteristics. The external quantum efficiency was determined as a function of current density. FIG. 3, and specifically plot 310, shows luminous efficiency v. luminance for a device having an emissive layer doped with compound 1 at 6% by weight. FIG. 4, and specifically plot 410, shows external quantum efficiency v. current density for a device having an emissive layer doped with compound 1 at 6% by weight. FIG. 5, and specifically plot 510, shows luminous efficiency v. luminance for a device having an emissive layer doped with compound 2 at 6% by weight. FIG. 6, and specifically plot 610, shows external quantum efficiency v. current density for a device having an emissive layer doped with compound 2 at 6% by weight.

Compound 2 has a structure similar to FIrpic, except that one of the ligands has been replaced with an ancillary ligand that, it is believed, blue shifts the emission of the material. In particular, FIrpic in solution emits light having CIE coordinates of (0.16, 0.32), and a device similar to the ones described above, but doped with FIrpic, instead of Compound 2 emits light having CIE coordinates of (0.16, 0.37). Compound 2 in solution emits light having CIE coordinates of (0.16, 0.27), and the device doped with Compound 2 emits light having CIE coordinates of (0.16, 0.32). The device including Compound 2 was less efficient than similar devices including FIrpic, but it may be acceptable to trade off some efficiency for a more saturated blue emission.

While the present invention is described with respect to particular examples and preferred embodiments, it is understood that the present invention is not limited to these examples and embodiments. The present invention as claimed therefore includes variations from the particular examples and preferred embodiments described herein, as will be apparent to one of skill in the art.

What is claimed is:
1. An emissive material comprising a compound having the formula:
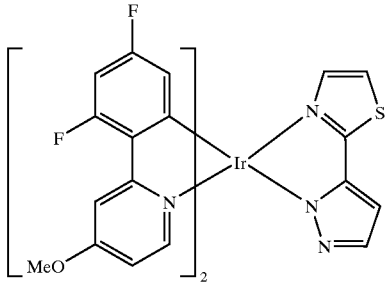
2. An organic light emitting device, comprising:
(a) an anode;
(b) a cathode;
(c) an emissive layer disposed between the anode and the cathode, the emissive layer including a material having a structure selected from the group consisting of:
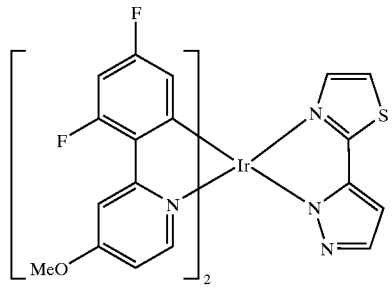
* * * * *